US010869826B2

(12) United States Patent
Sayer et al.

(10) Patent No.: US 10,869,826 B2
(45) Date of Patent: Dec. 22, 2020

(54) PARTICULATE METAL OXIDE PARTICLES COMPRISING A METAL OXIDE CORE AND A COATING LAYER COMPRISING AN INORGANIC MATERIAL, A SILANE COUPLING AGENT AND/OR A HYDROPHOBIZING AGENT

(71) Applicant: CRODA INTERNATIONAL PLC, Yorkshire (GB)

(72) Inventors: Robert Michael Sayer, Lancashire (GB); Ian Robert Tooley, Cheshire (GB); Paul Martin Staniland, Cheshire (GB)

(73) Assignee: Croda International PLC

(*) Notice: Subject to any disclaimer, the term of this patent is extended or adjusted under 35 U.S.C. 154(b) by 0 days.

(21) Appl. No.: 14/418,999

(22) PCT Filed: Jul. 19, 2013

(86) PCT No.: PCT/GB2013/051937
§ 371 (c)(1),
(2) Date: Feb. 2, 2015

(87) PCT Pub. No.: WO2014/023932
PCT Pub. Date: Feb. 13, 2014

(65) Prior Publication Data
US 2015/0209260 A1 Jul. 30, 2015

(30) Foreign Application Priority Data
Aug. 6, 2012 (GB) .................................. 1213962.2

(51) Int. Cl.
*A61K 8/58* (2006.01)
*A61K 8/29* (2006.01)
*A61Q 17/04* (2006.01)
*A61K 8/02* (2006.01)
*C09C 1/04* (2006.01)
*C09C 3/00* (2006.01)
*C09C 1/24* (2006.01)
*A61K 8/25* (2006.01)
*C09C 1/36* (2006.01)
*C09C 3/06* (2006.01)
*C09C 3/12* (2006.01)
*C09C 3/08* (2006.01)
*A61K 8/36* (2006.01)
*B82Y 30/00* (2011.01)
*A61K 8/04* (2006.01)

(52) U.S. Cl.
CPC ............ *A61K 8/585* (2013.01); *A61K 8/0241* (2013.01); *A61K 8/04* (2013.01); *A61K 8/25* (2013.01); *A61K 8/29* (2013.01); *A61K 8/361* (2013.01); *A61Q 17/04* (2013.01); *B82Y 30/00* (2013.01); *C09C 1/043* (2013.01); *C09C 1/24* (2013.01); *C09C 1/3661* (2013.01); *C09C 1/3669* (2013.01); *C09C 1/3676* (2013.01); *C09C 1/3692* (2013.01); *C09C 3/006* (2013.01); *C09C 3/063* (2013.01); *C09C 3/08* (2013.01); *C09C 3/12* (2013.01); *A61K 2800/413* (2013.01); *A61K 2800/63* (2013.01); *C01P 2004/51* (2013.01); *C01P 2004/64* (2013.01); *C01P 2004/84* (2013.01); *C01P 2006/12* (2013.01); *C01P 2006/60* (2013.01)

(58) Field of Classification Search
None
See application file for complete search history.

(56) References Cited

U.S. PATENT DOCUMENTS

| 6,126,915 | A | 10/2000 | Tunashima |
| 6,616,746 | B2 | 9/2003 | Takahashi |
| 6,773,814 | B2 | 8/2004 | Schumacher |
| 2002/0054999 | A1* | 5/2002 | Kessell ............... A61K 8/11 428/447 |
| 2003/0161805 | A1 | 8/2003 | Schlossman |
| 2003/0223940 | A1* | 12/2003 | Dransfield ............ A61K 8/25 424/59 |

(Continued)

FOREIGN PATENT DOCUMENTS

| EP | 1284277 | 2/2003 |
| EP | 1571180 | 9/2005 |
| EP | 1709124 | 10/2006 |
| JP | H09509686 A | 9/1997 |
| JP | 2001026423 | 1/2001 |
| JP | 2005255997 A | 9/2005 |
| JP | 2007016111 A | 1/2007 |

(Continued)

OTHER PUBLICATIONS

Diffey, B.L. et al., "A new substrate to measure sunscreen protection factors throughout the ultraviolet spectrum," 1989, pp. 127-133, vol. 40, Journal of the Society of Cosmetic Chemists.
Egerton, T, et al., "The surface characterisation of coated titanium dioxide by FTIR spectroscopy of adsorbed nitrogen," 2002, pp. 1111-1117, vol. 12, Journal of Materials Chemistry.
International Search Report for International Application No. PCT/GB2013/051937 dated Nov. 7, 2013.
Warren, B.E., "X-Ray Diffraction, b) The Method of Stokes and Wilson" Dover Publications, Inc., New York, reprint of Addison-Wesley Publishing Company, Inc., 1969, 11 pgs.
Notice of Reasons for Rejection for Japanese Application No. 2015-525934, dated May 23, 2017, 4 pages, English language translation;.

*Primary Examiner* — David J Blanchard
*Assistant Examiner* — Sarah J Chickos
(74) *Attorney, Agent, or Firm* — RatnerPrestia

(57) ABSTRACT

A particulate metal oxide has a metal oxide core and a coating layer containing an inorganic material and (i) a quaternary silane coupling agent, and/or (ii) a silane coupling agent and a hydrophobizing agent. Preferred materials are titanium dioxide core particles, an amino organosilane coupling agent and a fatty acid hydrophobizing agent. The particulate metal oxide is suitable for use in forming a dispersion, and the particles and dispersion can be used in an end-use sunscreen composition which is transparent, exhibits effective UV absorption properties, reduced photoactivity, and/or improved skin feel.

16 Claims, No Drawings

(56) References Cited

U.S. PATENT DOCUMENTS

| | | | |
|---|---|---|---|
| 2005/0020699 A1* | 1/2005 | Isobe | B41M 5/5218 516/33 |
| 2005/0197428 A1* | 9/2005 | May | C09C 1/3669 523/210 |
| 2008/0008757 A1* | 1/2008 | Kessell | A61K 8/27 424/486 |
| 2008/0057008 A1 | 3/2008 | Naden et al. | |
| 2009/0191273 A1* | 7/2009 | Kessell | A61K 8/26 424/489 |
| 2010/0090182 A1 | 4/2010 | Tooley et al. | |

FOREIGN PATENT DOCUMENTS

| | | |
|---|---|---|
| JP | 2007529483 A | 10/2007 |
| JP | 2009540092 A | 11/2009 |
| JP | 2010501707 A | 1/2010 |
| WO | 9523192 A1 | 8/1995 |
| WO | 2005099651 | 10/2005 |
| WO | 2007072008 | 6/2007 |
| WO | 2007144577 | 12/2007 |
| WO | 2008023073 | 2/2008 |
| WO | 2011025504 | 3/2011 |
| WO | 2011077084 | 6/2011 |

* cited by examiner

PARTICULATE METAL OXIDE PARTICLES COMPRISING A METAL OXIDE CORE AND A COATING LAYER COMPRISING AN INORGANIC MATERIAL, A SILANE COUPLING AGENT AND/OR A HYDROPHOBIZING AGENT

CROSS REFERENCE TO RELATED APPLICATIONS

This application is the U.S. National Phase application of PCT International Application No. PCT/GB2013/051937, filed Jul. 19, 2013, and claims priority of Great Britain Application No. 1213962.2, filed Aug. 6, 2012, the disclosures of which are incorporated herein by reference in their entireties for all purposes.

FIELD OF INVENTION

The present invention relates to metal oxide particles, a metal oxide dispersion, and in particular to the use thereof in a sunscreen product.

BACKGROUND

Metal oxides such as titanium dioxide, zinc oxide and iron oxide have been employed as attenuators of ultraviolet light in sunscreens. Due to the increased awareness of the link between ultraviolet light and skin cancer, there has been a requirement for ultraviolet light protection in everyday skincare and cosmetic products. There is a requirement for a metal oxide in a form which when incorporated into sunscreen products exhibits both effective UV absorption properties and be transparent in use.

In addition, metal oxides may be photoactive which can result in unwanted interactions with other ingredients in end use sunscreen products. Metal oxides normally need to be coated, e.g. with inorganic and/or organic coatings, in order to have acceptable photoactivity. Unfortunately, coatings which give acceptable photoactivity may have poor adhesion to the underlying metal oxide and be susceptible to being easily removed, e.g. during production, from the metal oxide particles. There is also a requirement for metal oxides to have improved skin feel when incorporated into end-use sunscreen and cosmetic products.

Thus, there is a need to provide a coated metal oxide with improved coating integrity, i.e. the coating remains adhered to the metal oxide, which is transparent, exhibits effective UV absorption properties, reduced photoactivity, and/or improved skin feel.

SUMMARY OF THE INVENTION

We have now surprisingly discovered an improved metal oxide, which overcomes or significantly reduces at least one of the aforementioned problems.

Accordingly, the present invention provides a particulate metal oxide comprising metal oxide core particles having a coating layer comprising an inorganic material and (i) a quaternary silane coupling agent, and/or (ii) a silane coupling agent and a hydrophobizing agent.

The present invention also provides a dispersion comprising a particulate metal oxide comprising metal oxide core particles having a coating layer comprising an inorganic material and (i) a quaternary silane coupling agent, and/or (ii) a silane coupling agent and a hydrophobizing agent, in a dispersing medium.

The present invention further provides a method of making metal oxide particles which comprises (i) forming metal oxide core particles, (ii) applying a coating layer to the core particles comprising an inorganic material, a silane coupling agent and a hydrophobizing agent.

The present invention still further provides a sunscreen composition comprising a particulate metal oxide comprising metal oxide core particles having a coating layer comprising an inorganic material and (i) a quaternary silane coupling agent, and/or (ii) a silane coupling agent and a hydrophobizing agent; and/or a dispersion comprising the particulate metal oxide in a dispersing medium.

The present invention yet further provides the use of a particulate metal oxide comprising metal oxide core particles having a coating layer comprising an inorganic material and (i) a quaternary silane coupling agent, and/or (ii) a silane coupling agent and a hydrophobizing agent, to give improved skin feel in a sunscreen composition.

The metal oxide of the basic or core particles preferably comprises an oxide of titanium, zinc or iron, and more preferably titanium dioxide or zinc oxide, and particularly titanium dioxide.

The metal oxide core particles may be prepared by standard procedures known in the art. The preferred titanium dioxide core particles may be prepared, for example, by the chloride or the sulphate process, or by hydrolysis of an appropriate titanium compound such as titanium oxydichloride or an organic or inorganic titanate, or by oxidation of an oxidisable titanium compound, e.g. in the vapour state. The titanium dioxide core particles are preferably prepared by the hydrolysis of a titanium compound, particularly of titanium oxydichloride.

The preferred titanium dioxide core particles comprise anatase and/or rutile crystal form. The titanium dioxide in the particles suitably comprises a major portion of rutile, preferably greater than 70%, more preferably greater than 80%, particularly greater than 90%, and especially greater than 95% by weight of rutile.

The metal oxide core particles may contain a substantially pure single metal oxide, e.g. titanium dioxide or zinc oxide, or may contain other metal oxides such as silica, alumina and/or zirconia. These other metal oxides may be incorporated into the particles for example, by co-oxidizing or co-precipitating, e.g. titanium compounds with other metal compounds. If co-oxidized or co-precipitated metals are present, they are preferably present as the metal oxide in the range from 0.05% to 20%, more preferably 0.2% to 5%, and especially 0.5% to 1.5% by weight based on the total weight of the metal oxide core particles.

The metal oxide core particles may be doped with a dopant metal selected from the group consisting of aluminium, chromium, cobalt, copper, gallium, iron, lead, manganese, nickel, silver, tin, vanadium, zinc, zirconium, and combinations thereof. The dopant is preferably selected from the group consisting of chromium, cobalt, copper, iron, manganese, nickel, silver, and vanadium, more preferably from chromium, manganese, and vanadium, and particularly manganese, and especially in the 3+ state.

Doping can be performed by normal methods known in the art. Doping is preferably achieved by co-precipitation of the metal oxide and a soluble dopant complex such as manganese chloride or manganese acetate. Alternatively doping can be performed by a baking technique by heating, for example, a metal complex in the presence of a dopant complex, e.g. manganese nitrate, at a temperature of greater than 500° C. and normally up to 1,000° C. Dopants can also be added by oxidizing a mixture containing a metal complex and dopant complex, e.g. manganese acetate, such as by spraying the mixture through a spray atomizer into an oxidation chamber.

When dopant is present, the metal oxide core particles preferably comprise in the range from 0.01% to 3%, more preferably 0.05% to 2%, particularly 0.1% to 1%, and especially 0.5% to 0.7% by weight of dopant metal, preferably manganese, based on the total weight of metal oxide core particles.

The inorganic material of the coating layer is chemically different to the metal oxide, preferably titanium dioxide, of the core particles. The inorganic material may comprise oxides of other elements such as oxides of aluminium, zirconium, cerium, zinc (when the core particles are not zinc oxide) and/or silicon, preferably of silicon and/or aluminium, and particularly of silicon.

The inorganic material is suitably attached to the surface of the metal oxide core particles, preferably by covalent bonds. Thus, the inorganic material is preferably in the form of an inner coating layer that is directly in contact with the outer surface of the core particles. The inorganic material may completely surround or encapsulate the surface of the core particle, but preferably does not form a complete coating and areas of the surface of the metal oxide core particles are not coated by the inorganic material and are still exposed.

The inorganic material is suitably present in the coating layer in the range from 0.5% to 35%, preferably 2% to 25%, more preferably 4% to 20%, particularly 6% to 15%, and especially 7% to 11% by weight based on the weight of metal oxide core particles.

In one embodiment, the inorganic material comprises, consists essentially of, or consists of silica. The amount of silica in the coating layer is suitably in the range from 2% to 25%, preferably 4% to 20%, more preferably 6% to 15%, particularly 8% to 12%, and especially 9% to 11% by weight based on the weight of metal oxide core particles. The silica may be applied using techniques known in the art. A typical process comprises forming an aqueous dispersion of metal oxide particles in the presence of a soluble salt of silica. This dispersion is preferably alkali, more preferably having a pH of greater than 8, and particularly in the range from 9 to 12. The precipitation of the silica is achieved by adjusting the pH of the dispersion by the addition of acid or alkali, as appropriate. The silica is preferably amorphous, and more preferably is in a highly hydrated form, i.e. contains a high proportion of hydroxyl groups. The silica is preferably not in the form of dense silica.

In another embodiment, the inorganic material comprises, consists essentially of, or consists of aluminium oxide and/or aluminium hydroxide (hereinafter both referred to as alumina). The amount of alumina in the coating layer is preferably in the range from 1% to 20%, more preferably 3% to 14%, particularly 6% to 11%, and especially 7% to 9% by weight based on the weight of metal oxide core particles.

Alumina can be formed in the coating layer by adding aluminium sulphate and/or a metal aluminate, preferably water soluble, to the dispersion of metal oxide core particles. Sodium aluminate is a particularly preferred metal aluminate. Precipitation of alumina on the surface of the metal oxide core particles can also be achieved by suitable control of pH.

The inorganic material may comprise, consist essentially of, or consist of a mixture of both silica and alumina. The amount of silica in the silica/alumina containing coating layer is suitably in the range from 5% to 25%, preferably 7% to 20%, more preferably 8% to 15%, particularly 9% to 12%, and especially 10% to 11% by weight based on the weight of metal oxide core particles. The amount of alumina in the silica/alumina containing coating layer is preferably in the range from 1% to 20%, more preferably 3% to 14%, particularly 6% to 11%, and especially 7% to 9% by weight based on the weight of metal oxide core particles.

In one embodiment, the inorganic material comprises phosphate. The preferred amount of phosphate in the coating layer is in the range from 0.1% to 12%, more preferably 0.5% to 6%, particularly 1% to 3%, and especially 1.5% to 2.5% by weight of phosphorous, based on the weight of metal oxide core particles. The phosphate containing coating layer may be formed by adding a, preferably water soluble, phosphate or salt of phosphoric acid to a dispersion, normally aqueous, to metal oxide core particles. Suitable water soluble phosphates include metal, preferably alkali metal, or ammonium phosphates such mono-, di- or tri-sodium phosphate, mono-, di- or tri-potassium phosphate or alternatively a polymeric phosphate, such as a polymeric alkali metal phosphate, for example tri-sodium polyphosphate or sodium hexametaphosphate. Polymeric phosphates are preferred, particularly sodium hexametaphosphate. Phosphate is preferably precipitated with a suitable cation, preferably metal, on to the surface of the metal oxide core particles. Suitable metal cations include aluminium, zirconium and cerium, and preferably aluminium. The precipitation of the phosphate, preferably metal phosphate, and particularly aluminium phosphate, can be achieved by adjusting the pH of the dispersion by the addition of acid or alkali, as appropriate.

The amount of the preferred metal, particularly aluminium, in the phosphate coating layer is preferably in the range from 0.2% to 20%, more preferably 1.5% to 10%, particularly 3% to 7%, and especially 4% to 5% by weight based on the weight of metal oxide core particles.

The preferred metal compound, more preferably water soluble, particularly in the form of a salt such as a sulphate or oxide, preferably sulphate, can be added together with the phosphate to the dispersion of metal oxide core particles. The phosphate coating layer may be formed by adding sodium hexametaphosphate and aluminium sulphate to an aqueous slurry or dispersion of metal oxide core particles, and the pH adjusted in order to achieve precipitation of aluminium phosphate. The phosphate coating layer may additionally comprise alumina, as described herein.

The silane coupling agent comprises at least one hydrolysable group, at least one functional group and an optional linking group(s). The silane coupling agent preferably comprises 2 or 3, more preferably 3, hydrolysable groups; 1 or 2, more preferably 1 functional group; and 1 or 2, more preferably 1 linking group. The silane coupling agent is suitably an organosilane, and preferably is of general Formula (1);

$$X_{4-n}\text{—Si-}[L_m\text{-Y}]_n \qquad (1)$$

wherein
Y is a functional group,
X is a hydrolysable group,
L is a linking group,
m is 0 or 1, preferably 1, and
n is 1 or 2, preferably 1.

Thus, a preferred silane coupling agent is of the general formula $X_3$—Si-L-Y. The at least one functional group (Y) may be, for example, selected from the group consisting of methyl, ethyl, vinyl, carboxyl, glycidoxy, epoxy, glycidyl, amino, mercapto, acrylic, and methacrylic group. The functional group preferably comprises a nitrogen atom, and more preferably is an amine group. The amine group may be a primary, secondary, tertiary or quaternary group, and is preferably a primary amine group.

The preferred amine group is suitably of formula —$NR_2$, wherein each R individually is, or comprises, a group selected from the group consisting of hydrogen, lower (i.e. C1-C6) alkyl, aryl, lower alkylaryl, lower arylalkyl, alkenyl, cycloalkenyl, alkene, alkylene, arylene, alkylarylene, arylalkylene and cycloalkylene. In a preferred embodiment, each R is individually selected from the group consisting of hydrogen and a linear or branched C1-C6 alkyl group, more preferably hydrogen and a C1-C4 alkyl group, and particularly where both R groups are hydrogen.

The at least one hydrolysable group (X) may be —$OR^1$, —Cl, —Br, —I, and preferably is —$OR^1$, wherein each $R^1$ individually is, or comprises, a group selected from the group consisting of hydrogen, lower (i.e. C1-C6) alkyl, aryl, lower alkylaryl, lower arylalkyl, alkenyl, cycloalkenyl, alkene, alkylene, arylene, alkylarylene, arylalkylene and cycloalkylene. Preferably each $R^1$ is individually selected from the group consisting of hydrogen and a linear or branched C1-C6 alkyl group, more preferably a C1-C4 alkyl, particularly a C1-C2 alkyl group, and especially an ethyl group.

The optional linking group (L) may comprise or consist of an alkyl, aryl, alkylaryl, arylalkyl, cycloalkyl, alkenyl, cycloalkenyl, alkene, alkenylene, cycloalkenylene, alkylene, arylene, alkylarylene, arylalkylene, and/or cycloalkylene group. The linking group is preferably a linear or branched C1-C6 alkylene group, more preferably a C1-C4 alkylene group, and particularly a C3 alkylene, i.e. propyl, group.

Examples of suitable silane coupling agents include methyl trimethoxysilane, glycidoxypropyl trimethoxysilane, methacryloxypropyltri-methoxysilane, vinyl triethoxysilane, phenyl alkoxysilanes such as phenyl trialkoxysilane and diphenyl dialkoxysilane, dialkyl dialkoxysilanes such as dimethyl dimethoxysilane and dimethyl diethoxysilane, quaternary silanes, and amino silanes.

Amino silanes are preferred and suitable materials include aminoethyl trimethoxysilane, aminoethyl triethoxysilane, aminopropyl trimethoxysilane, aminopropyl triethoxysilane, methylaminopropyl trimethoxysilane, ethylaminopropyl trimethoxysilane, aminopropyl tripropoxysilane, aminoisobutyl trimethoxysilane, and aminobutyl triethoxysilane. An especially preferred amino silane is aminopropyl triethoxysilane ($NH_2$—$CH_2CH_2CH_2$—Si—$[OCH_2CH_3]_3$).

The amount of silane coupling agent, or reaction product thereof, present in the coating layer is suitably in the range from 0.5% to 20%, preferably 2% to 14%, more preferably 3% to 10%, particularly 4% to 9%, and especially 5% to 8% by weight based on the weight of metal oxide core particles.

The quaternary silane coupling agent is suitably of general Formula (2);

wherein
X, L and m are as defined in Formula (1) above,
each $R^2$ is individually a lower (i.e. C1-C6) alkyl, preferably C1-C4 alkyl, more preferably C1-C2 alkyl, and particularly a methyl group,
$R^3$ is a hydrocarbyl, preferably alkyl or alkenyl, more preferably alkyl, group which may be branched or linear, preferably linear, comprising greater than 6, preferably greater than 10 carbon atoms, more preferably in the range from 12 to 40, particularly 14 to 24, and especially 16 to 20 carbon atoms, and
$Z^-$ is an anion, preferably a monovalent anion, more preferably selected from the group consisting of halide ions, such as bromide, iodide, chloride, and alkyl sulfate, such as methyl or ethyl sulphate. $Z^-$ is preferably a halide ion, more preferably a chloride ion.

Specific examples of suitable quaternary silane coupling agents include those selected from the group consisting of dimethyloctadecyl[3-(trimethoxysilyl)propyl]ammonium chloride, dimethyloctadecyl[3-(triethoxysilyl)propyl]ammonium chloride, dimethyloctadecyl[3-(trimethoxysilyl)propyl]ammonium bromide, didecylmethyl[3-(trimethoxysilyl)propyl]ammonium chloride, dimethyltetradecyl[3-(trimethoxysilyl)propyl]ammonium chloride, dimethyltetradecyl[3-(trimethoxysilyl)propyl]ammonium bromide, and dimethylhexadecyl[3-(trimethoxysilyl)propyl]ammonium chloride.

The amount of quaternary silane coupling agent, or reaction product thereof, present in the coating layer is suitably in the range from 1% to 30%, preferably 5% to 25%, more preferably 8% to 20%, particularly 11% to 16%, and especially 13% to 14% by weight based on the weight of metal oxide core particles.

The silane coupling agent and/or quaternary silane coupling agent may be applied using any conventional process. Suitably, metal oxide particles, preferably coated with inorganic material as described herein, are dispersed in water and heated to a temperature in the range from 50° C. to 80° C., after which the coupling agent is added and reacts with the surface of the inorganic material and/or the surface of the metal oxide core particles.

The hydrophobizing agent used to form the coating layer is a water-repellent material, preferably organic, and suitable materials include fatty acids, fatty alcohols, e.g. stearyl alcohol, and silicones such as polydimethylsiloxane and substituted polydimethylsiloxanes, and reactive silicones such as methylhydrosiloxane and polymers and copolymers thereof. The hydrophobizing agent suitably comprises a hydrocarbyl, preferably an alkyl or alkenyl, more preferably an alkyl, group comprising greater than 6, preferably greater than 10, more preferably in the range from 12 to 100, particularly 14 to 50, and especially 16 to 20 carbon atoms.

The hydrophobizing agent is preferably a fatty acid and/or salt thereof comprising 10 to 24, more preferably 12 to 22, particularly 14 to 20, and especially 16 to 18 carbon atoms. The fatty chain may be linear or branched, is preferably saturated, and suitable fatty acids include lauric acid, myristic acid, palmitic acid, stearic acid, isostearic acid, arachidic acid, behenic acid and mixtures thereof. Palmitic acid and/or stearic acid are preferred, and particularly stearic acid.

The amount of hydrophobizing agent, or reaction product thereof, present in the coating layer is suitably in the range from 0.5% to 20%, preferably 2% to 15%, more preferably 4% to 12%, particularly 5% to 10%, and especially 6% to 8% by weight based on the weight of metal oxide core particles.

The hydrophobizing agent may be applied using any conventional process. Typically, metal oxide particles, preferably coated with both inorganic material and silane coupling agent as described herein, are dispersed in water and heated to a temperature in the range from 50° C. to 80° C. The hydrophobizing agent, e.g. a fatty acid, for example, is then deposited on the metal oxide particles by adding a salt of the fatty acid (e.g. sodium stearate) to the suspension, followed by an acid. Alternatively, the metal oxide particles can be mixed with a solution of the hydrophobizing agent in an organic solvent, followed by evaporation of the solvent. In an alternative embodiment of the invention, the hydrophobizing agent can be added directly to the composition used to form the metal oxide particles, i.e. during the preparation thereof, such that the hydrophobic coating is formed in situ.

The entire coating process is preferably carried out using an aqueous slurry method, by modifying the pH and temperature at each stage of the process. The method may be carried out using a multi-stage process. An aqueous solution containing the inorganic material may be added to an aqueous slurry of metal oxide core particles at alkaline pH and elevated temperature. The quaternary silane coupling agent and/or silane coupling agent and hydrophobizing agent may be subsequently added to the slurry at the elevated temperature and pH in one or two further stages, in the same reaction vessel. The coating components are preferably applied in the order of 1) inorganic material, 2) silane coupling agent, and 3) hydrophobizing agent or 1) inorganic material, and 2) quaternary silane coupling agent.

In one preferred embodiment, the metal oxide particles according to the present invention comprise (i) in the range from 79% to 87%, more preferably 81% to 85%, particularly 82% to 84%, and especially 82.5% to 83.5% by weight of metal oxide, preferably titanium dioxide, (ii) in the range from 4% to 10%, more preferably 5.5% to 8.5%, particularly 6.5% to 7.5%, and especially 6.7% to 7.3% by weight of inorganic material, preferably silica, (iii) in the range from 1.5% to 8%, more preferably 3% to 6.5%, particularly 4% to 5.5%, and especially 4.5% to 5% by weight of the reaction product of a silane coupling agent, preferably an amino silane, and (iv) in the range from 2% to 8.5%, more preferably 3.5% to 7%, particularly 4.5% to 6%, and especially 5% to 5.5% by weight of the reaction product of a hydrophobizing agent, preferably a C10 to C24 fatty acid, all based on the total dry weight of the particles.

The particles of metal oxide of the present invention are preferably hydrophobic. The hydrophobicity of the metal oxide can be determined by pressing a disc of metal oxide powder, and measuring the contact angle of a drop of water placed thereon, by standard techniques known in the art. The contact angle of the hydrophobic metal oxide particles is preferably greater than 30°, more preferably greater than 35°, and particularly greater than 40°.

In one embodiment, the individual or primary coated metal oxide particles are preferably acicular in shape and have a long axis (maximum dimension or length) and short axis (minimum dimension or width). The third axis of the particles (or depth) is preferably approximately the same dimensions as the width.

The mean length by number of the primary metal oxide particles is suitably less than 125 nm, preferably in the range from 50 to 90 nm, more preferably 55 to 77 nm, particularly 60 to 70 nm, and especially 60 to 65 nm. The mean width by number of the particles is suitably less than 25 nm, preferably in the range from 5 to 20 nm, more preferably 10 to 18 nm, particularly 12 to 17 nm, and especially 14 to 16 nm. The primary metal oxide particles preferably have a mean aspect ratio $d_1:d_2$ (where $d_1$ and $d_2$, respectively, are the length and width of the particle) in the range from 2.0 to 8.0:1, more preferably 3.0 to 6.5:1, particularly 4.0 to 6.0:1, and especially 4.5 to 5.5:1. The size of the primary particles can be suitably measured using electron microscopy. The size of a particle can be determined by measuring the length and width of a primary particle selected from a photographic image obtained by using a transmission electron microscope.

The primary metal oxide particles suitably have a median volume particle diameter (equivalent spherical diameter corresponding to 50% of the volume of all the particles, read on the cumulative distribution curve relating volume % to the diameter of the particles—often referred to as the "D(v, 0.5)" value), measured as herein described, of less than 45 nm, preferably in the range from 25 to 35 nm, more preferably 27 to 33 nm, particularly 28 to 32 nm, and especially 29 to 31 nm.

The coated metal oxide particles suitably have a mean crystal size (measured by X-ray diffraction as herein described) of less than 16 nm, preferably in the range from 5 to 14 nm, more preferably 7 to 11 nm, particularly 8 to 10 nm, and especially 8.5 to 9.5 nm.

The size distribution of the crystal size of the metal oxide particles can be important, and suitably at least 30%, preferably at least 40%, more preferably at least 50%, particularly at least 60%, and especially at least 70% by weight of the metal oxide particles have a crystal size within one or more of the above preferred ranges for the mean crystal size.

When formed into a dispersion, the particulate coated metal oxide according to the invention suitably has a median volume particle diameter (equivalent spherical diameter corresponding to 50% of the volume of all the particles, read on the cumulative distribution curve relating volume % to the diameter of the particles—often referred to as the "D(v, 0.5)" value)) (hereinafter referred to as dispersion particle size), measured as herein described, of less than 85 nm, preferably in the range from 30 to 65 nm, more preferably 40 to 55 nm, particularly 44 to 50 nm, and especially 46 to 48 nm.

The size distribution of the metal oxide particles in dispersion can also be an important parameter in obtaining the required properties. In a preferred embodiment suitably less than 10% by volume of metal oxide particles have a volume diameter of more than 30 nm, preferably more than 24 nm, more preferably more than 20 nm, particularly more than 16 nm, and especially more than 12 nm below the median volume particle diameter. In addition, suitably less than 16% by volume of metal oxide particles have a volume diameter of more than 27 nm, preferably more than 21 nm, more preferably more than 17 nm, particularly more than 13 nm, and especially more than 9 nm below the median volume particle diameter. Further, suitably less than 30% by volume of metal oxide particles have a volume diameter of more than 16 nm, preferably more than 13 nm, more preferably more than 10 nm, particularly more than 8 nm, and especially more than 6 nm below the median volume particle diameter.

Also, suitably more than 90% by volume of metal oxide particles have a volume diameter of less than 400 nm, preferably less than 300 nm, more preferably less than 250 nm, particularly less than 230 nm, and especially less than 200 nm above the median volume particle diameter. In addition, suitably more than 84% by volume of metal oxide particles have a volume diameter of less than 70 nm, preferably less than 50 nm, more preferably less than 35 nm, particularly less than 30 nm, and especially less than 25 nm above the median volume particle diameter. Further, suitably more than 70% by volume of metal oxide particles have a volume diameter of less than 24 nm, preferably less than 18 nm, more preferably less than 14 nm, particularly less than 10 nm, and especially less than 6 nm above the median volume particle diameter.

Dispersion particle size of the coated metal oxide particles may be measured by electron microscopy, coulter counter, sedimentation analysis and static or dynamic light scattering. Techniques based on sedimentation analysis are preferred. The median particle size may be determined by plotting a cumulative distribution curve representing the percentage of particle volume below chosen particle sizes and measuring the 50th percentile. The median volume particle diameter and particle size distribution of the metal oxide particles in dispersion is suitably measured using a Brookhaven particle sizer, as described herein.

In another embodiment, the individual or primary, preferably calcined, coated metal oxide, preferably titanium dioxide, particles according to the invention suitably have a mean aspect ratio $d_1:d_2$ (where $d_1$ and $d_2$, respectively, are the length and width of the particle) in the range from 1.0 to 2.5:1, preferably 1.2 to 2.0:1, more preferably 1.3 to 1.8:1, particularly 1.4 to 1.6:1, and especially 1.45 to 1.55:1. The mean length by number of the metal oxide particles is suitably in the range from 30 to 75 nm, preferably 36 to 68 nm, more preferably 42 to 62 nm, particularly 47 to 57 nm, and especially 50 to 54 nm. The mean width by number of the particles is suitably in the range from 20 to 55 nm, preferably 25 to 48 nm, more preferably 28 to 42 nm, particularly 31 to 38 nm, and especially 33 to 36 nm. The size of these primary particles can also be determined by measuring the length and width of particles selected from a photographic image obtained by using a transmission electron microscope.

These, preferably calcined, metal oxide particles suitably have (i) a mean crystal size (measured by X-ray diffraction as herein described) in the range from 15 to 45 nm, preferably 20 to 40 nm, more preferably 25 to 35 nm, particularly 28 to 33 nm, and especially 30 to 31 nm, and/or (ii) a median volume particle diameter (equivalent spherical diameter corresponding to 50% of the volume of all the particles, read on the cumulative distribution curve relating volume % to the diameter of the particles—often referred to as the "D(v, 0.5)" value)) in dispersion, measured as herein described, of greater than 70 nm, preferably in the range from 85 to 175 nm, more preferably 100 to 160 nm, particularly 115 to 150 nm, and especially 125 to 140 nm.

In a particularly preferred embodiment of the invention, the coated metal oxide particles according to the invention have a BET specific surface area, measured as described herein, of greater than 50, more preferably in the range from 60 to 120, particularly 75 to 100, and especially 85 to 90 $m^2g^{-1}$.

The coated metal oxide particles of the present invention are transparent, suitably having an extinction coefficient at 524 nm ($E_{524}$), measured as described herein, of less than 2.0, preferably in the range from 0.5 to 1.6, more preferably 0.7 to 1.4, particularly 0.9 to 1.3, and especially 1.0 to 1.21/g/cm. In addition, the metal oxide particles suitably have an extinction coefficient at 450 nm ($E_{450}$), measured as described herein, in the range from 1.0 to 2.6, preferably 1.4 to 2.4, more preferably 1.6 to 2.3, particularly 1.8 to 2.2, and especially 1.9 to 2.11/g/cm.

The coated metal oxide particles exhibit effective UV absorption, suitably having an extinction coefficient at 360 nm ($E_{360}$), measured as described herein, in the range from 2 to 15, preferably 5 to 12, more preferably 7 to 10, particularly 8 to 9.5, and especially 8.5 to 9.01/g/cm. The metal oxide particles also suitably have an extinction coefficient at 308 nm ($E_{308}$), measured as described herein, in the range from 38 to 55, preferably 40 to 52, more preferably 42 to 50, particularly 44 to 48, and especially 45 to 47 l/g/cm.

The coated metal oxide particles suitably have a maximum extinction coefficient E(max), measured as described herein, in the range from 50 to 68, preferably 53 to 64, more preferably 55 to 62, particularly 56 to 60, and especially 57 to 59 l/g/cm. The metal oxide particles suitably have a λ(max), measured as described herein, in the range from 265 to 290, preferably 270 to 285, more preferably 272 to 282, particularly 274 to 280, and especially 276 to 278 nm.

The coated metal oxide particles suitably have an $E_{308}/E_{524}$ ratio of greater than 15, preferably greater than 20, more preferably in the range from 25 to 70, particularly 30 to 50, and especially 35 to 40.

The coated metal oxide particles suitably exhibit reduced whiteness, having a change in whiteness ΔL of a dispersion containing the particles, measured as herein described, of less than 7, preferably in the range from 1 to 6, more preferably 2 to 5, and particularly 3 to 4. In addition, the metal oxide particles preferably have a whiteness index, measured as herein described, of less than 100%, more preferably in the range from 20 to 80%, particularly 30 to 70%, and especially 40 to 60%.

The coated metal oxide particles preferably have reduced photoactivity, suitably having a photogreying index, measured as herein described, of less than 9, preferably in the range from 0.5 to 7, more preferably 1.5 to 5, particularly 2.5 to 4, and especially 3.0 to 3.5.

The particulate metal oxide according to the present invention may be in the form of a free-flowing powder. A powder having the required particle size may be produced by milling processes known in the art. The final milling stage of the metal oxide is suitably carried out in dry, gas-borne conditions to reduce aggregation. A fluid energy mill can be used in which the aggregated metal oxide powder is continuously injected into highly turbulent conditions in a confined chamber where multiple, high energy collisions occur with the walls of the chamber and/or between the aggregates. The milled powder is then carried into a cyclone and/or bag filter for recovery. The fluid used in the energy mill may be any gas, cold or heated, or superheated dry steam.

The particulate metal oxide may be formed into a slurry, or preferably a liquid dispersion, in any suitable aqueous or organic liquid medium. By liquid dispersion is meant a true dispersion, i.e. where the solid particles are stable to agglomeration. The particles in the dispersion are relatively uniformly dispersed and resistant to settling out on standing, but if some settling out does occur, the particles can be easily redispersed by simple agitation.

Cosmetically acceptable materials are preferred as the liquid medium. A useful organic medium is a liquid oil such as vegetable oils, e.g. fatty acid glycerides, fatty acid esters and fatty alcohols. One preferred organic medium is a siloxane fluid, especially a cyclic oligomeric dialkylsiloxane, such as the cyclic pentamer of dimethylsiloxane known as cyclomethicone. Alternative fluids include dimethylsiloxane linear oligomers or polymers having a suitable fluidity and phenyltris(trimethylsiloxy)silane (also known as phenyltrimethicone).

Examples of suitable organic media include non-polar materials such as C13-14 isoparaffin, isohexadecane, paraffinum liquidum (mineral oil), squalane, squalene, hydrogenated polyisobutene, and polydecene; and polar materials such as C12-15 alkyl benzoate, caprylic/capric triglyceride, cetearyl isononanoate, ethylhexyl isostearate, ethylhexyl palmitate, isononyl isononanoate, isopropyl isostearate, isopropyl myristate, isostearyl isostearate, isostearyl neopentanoate, octyldodecanol, pentaerythrityl tetraisostearate, PPG-15 stearyl ether, triethylhexyl triglyceride, dicaprylyl carbonate, ethylhexyl stearate, *Helianthus annus* (sunflower) seed oil, isopropyl palmitate, and octyldodecyl neopentanoate.

The dispersion according to the present invention may also contain a dispersing agent in order to improve the properties thereof. The dispersing agent is suitably present in the range from 1% to 30%, preferably 5% to 25%, more preferably 10% to 22%, particularly 14% to 20%, and especially 16% to 18% by weight based on the total weight of metal oxide particles.

Suitable dispersing agents include substituted carboxylic acids, soap bases and polyhydroxy acids. Typically the dispersing agent can be one having a formula X.CO.AR in which A is a divalent bridging group, R is a primary secondary or tertiary amino group or a salt thereof with an acid or a quaternary ammonium salt group and X is the residue of a polyester chain which together with the —CO— group is derived from a hydroxy carboxylic acid of the formula HO—R'—COOH. The dispersing agent may be a polyglycerol ester. As examples of typical dispersing agents are those based on ricinoleic acid, hydroxystearic acid, hydrogenated castor oil fatty acid which contains in addition to 12-hydroxystearic acid small amounts of stearic acid and palmitic acid. Dispersing agents based on one or more polyesters or salts of a hydroxycarboxylic acid and a carboxylic acid free of hydroxy groups can also be used. Compounds of various molecular weights can be used.

Other suitable dispersing agents are those monoesters of fatty acid alkanolamides and carboxylic acids and their salts. Alkanolamides are based on ethanolamine, propanolamine or aminoethyl ethanolamine for example. Alternative dispersing agents are those based on polymers or copolymers of acrylic or methacrylic acids, e.g. block copolymers of such monomers. Other dispersing agents of similar general form are those having epoxy groups in the constituent radicals such as those based on the ethoxylated phosphate esters. The dispersing agent can be one of those commercially referred to as a hyper dispersant.

Polyglyceryl-3 polyricinoleate and polyhydroxystearic acid are preferred dispersing agents. Polyglyceryl-3 polyricinoleate is particularly preferred.

An advantage of the present invention is that dispersions can be produced which contain at least 30%, preferably at least 35%, more preferably at least 40%, particularly at least 45%, especially at least 50%, and generally up to 60% by weight of metal oxide particles based on the total weight of the dispersion.

A composition, preferably a sunscreen product, containing the coated metal oxide particles according to the present invention suitably has a Sun Protection Factor (SPF), measured as herein described, of greater than 10, preferably greater than 15, more preferably greater than 20, particularly greater than 25, and especially greater than 30 and up to 40.

The coated metal oxide particles and dispersions of the present invention are useful as ingredients for preparing sunscreen compositions or end-use products, especially in the form of oil-in-water or water-in-oil emulsions. The compositions may further contain conventional additives suitable for use in the intended application, such as conventional cosmetic ingredients used in sunscreens. The particulate metal oxide as defined herein, may provide the only ultraviolet light attenuators in a sunscreen product according to the invention, but other sunscreening agents, such as other metal oxides and/or other organic materials may also be added. For example, the preferred titanium dioxide particles defined herein may be used in combination with other existing commercially available titanium dioxide and/or zinc oxide sunscreens.

A sunscreen composition containing the metal oxide particles according to the invention exhibits improved skin feel compared to conventional sunscreen compositions containing metal oxide. Such conventional sunscreen products exhibit a predominantly "waxy" skin feel, with a low degree of lubricity. Sunscreen compositions according to the invention have surprisingly improved skin feel, measured as herein described, for example conferring a significantly higher degree of lubricity to the skin.

The metal oxide particles and dispersions described herein are suitable for using in combination with organic UV absorbers such as butyl methoxydibenzoylmethane (avobenzone), benzophenone-3 (oxybenzone), 4-methylbenzylidene camphor (enzacamene), benzophenone-4 (sulisobenzone), bis-ethylhexyloxyphenol methoxyphenyl triazine (bemotrizinol), diethylamino hydroxybenzoyl hexyl benzoate, diethylhexyl butamido triazone, disodium phenyl dibenzimidazole tetrasulfonate, drometrizole trisiloxane, ethylhexyl dimethyl PABA (padimate O), ethylhexyl methoxycinnamate (octinoxate), ethylhexyl salicylate (octisalate), ethylhexyl triazone, homosalate, isoamyl p-methoxycinnamate (amiloxate), isopropyl methoxycinnamate, menthyl anthranilate (meradimate), methylene bis-benzotriazolyl tetramethylbutylphenol (bisoctrizole), octocrylene, PABA (aminobenzoic acid), phenylbenzimidazole sulfonic acid (ensulizole), terephthalylidene dicamphor sulfonic acid, and mixtures thereof. Preferred organic UV absorbers are butyl methoxydibenzoylmethane and benzophenone-3, and particularly butyl methoxydibenzoylmethane.

In this specification the following test methods have been used:

1) Crystal Size Measurement of Metal Oxide Particles

Crystal size was measured by X-ray diffraction (XRD) line broadening. Diffraction patterns were measured with Cu Kα radiation in a Siemens D5000 diffractometer equipped with a Sol-X energy dispersive detector acting as a monochromator. Programmable slits were used to measure diffraction from a 12 mm length of specimen with a step size of 0.02° and step counting time of 3 sec. The data was analysed by fitting the diffraction pattern between 22 and 48° 2θ with a set of peaks corresponding to the reflection positions for rutile and, where anatase was present, an additional set of peaks corresponding to those reflections. The fitting process allowed for removal of the effects of instrument broadening on the diffraction line shapes. The value of the weight average mean crystal size was determined for the rutile 110 reflection (at approximately 27.4° 2θ) based on its integral breadth according to the principles of the method of Stokes and Wilson (B. E. Warren, "X-Ray Diffraction", Addison-Wesley, Reading, Mass., 1969, pp 254-257).

2) Median Volume Particle Diameter and Particle Size Distribution of Metal Oxide Particles in Dispersion A dispersion of metal oxide particles was produced by mixing 7 g of polyglyceryl-3 polyricinoleate with 53 g of C12-C15 alkylbenzoate, and then adding 40 g of metal oxide powder into the solution. The mixture was passed through a horizontal bead mill, operating at approximately 2100 r.p.m. and containing zirconia beads as grinding media for 15 minutes. The dispersion of metal oxide particles was diluted to 2% by weight of solids by mixing with isopropyl myristate (it is necessary to ensure that the diluted dispersion is stable prior to measuring particle size (if necessary, more polyglyceryl-3 polyricinoleate may be added)). The diluted sample was analysed on the Brookhaven BI-XDC particle sizer in centrifugation mode, and the median volume particle diameter and particle size distribution determined, using the theoretical density (e.g. of titanium dioxide) of the particles.

3) BET Specific Surface Area of Metal Oxide Particles

The single point BET specific surface area was measured using a Micromeritics Flowsorb II 2300.

4) Change in Whiteness and Whiteness Index

A sunscreen formulation was coated on to the surface of a glossy black card and drawn down using a No 2 K bar to form a film of 12 microns wet thickness. The film was allowed to dry at room temperature for 10 minutes and the whiteness of the coating on the black surface ($L_F$) measured using a Minolta CR300 colourimeter. The change in whiteness $\Delta L$ was calculated by subtracting the whiteness of the substrate ($L_S$) from the whiteness of the coating ($L_F$). The whiteness index is the percentage change in whiteness $\Delta L$ compared to a standard titanium dioxide (=100% value) (Tayca MT100T (ex Tayca Corporation)).

5) Photogreying Index

A metal oxide dispersion was prepared by milling 15 g of metal oxide powder into 85 g of C12-15 alkyl benzoate for 15 min at 5000 rpm with a mini-motor mill (Eiger Torrance MK M50 VSE TFV), 70% filled with 0.8-1.25 mm zirconia beads (ER120SWIDE). Freshly milled dispersions were loaded into a 16 mm diameter×3 mm deep recess in 65×30×6 mm acrylic cells. A quartz glass cover slip was placed over the sample to eliminate contact with the atmosphere, and secured in place by a brass catch. Up to 12 cells could be placed on a rotating platform, positioned 12 cm from a 75 W UV light source (Philips HB 171/A with 4 TL29D16/09N lamps) and irradiated for 120 minutes. Sample colour (L*a*b* value) was recorded by a commercial colour meter (Minolta chroma meter CR-300), previously calibrated with a standard white tile (L*=97.95). The change in whiteness $\Delta L^*$ was calculated by subtracting the whiteness of the substrate before exposure to UV light ($L^*_{Initial}$) from the whiteness of the substrate after exposure to UV light. The photogreying index $\Delta L^* = L^*_{(Initial)} - L^*_{(120\ min)}$.

6) Sun Protection Factor

The Sun Protection Factor (SPF) of a sunscreen formulation was determined using the in vitro method of Diffey and Robson, J. Soc. Cosmet. Chem. Vol. 40, pp 127-133, 1989.

7) Extinction Coefficients

A 0.1 g sample of a metal oxide dispersion was diluted with 100 ml of cyclohexane. This diluted sample was then further diluted with cyclohexane in the ratio sample:cyclohexane of 1:19. The total dilution was 1:20,000. The diluted sample was then placed in a spectrophotometer (Perkin-Elmer Lambda 2 UV/VIS Spectrophotometer) with a 1 cm path length and the absorbance, of UV and visible light measured. Extinction coefficients were calculated from the equation A=E.c.l, where A=absorbance, E=extinction coefficient in litres per gram per cm, c=concentration in grams per litre, and l=path length in cm.

8) Skin Feel

Skin feel was measured by trained assessors, using a protocol in which test samples were assigned % numerical scores for a series of sensory attributes. 2 ml of the emulsion was spread over a circular area, approximately 5 cm in diameter, on the inner forearm. After spreading, the afterfeel of the test sample on the skin was characterized in the following terms:—% "oily" skin feel; % "waxy" skin feel; % "greasy" skin feel; and % "silicone" skin feel.

The invention is illustrated by the following non-limiting examples.

EXAMPLES

Example 1

1 mole of titanium oxydichloride in acidic solution was reacted with 3 moles of NaOH in aqueous solution. After the initial reaction period, the temperature was increased to above 70° C., and stirring continued. The reaction mixture was neutralised by the addition of aqueous NaOH, and allowed to cool below 70° C. Upon cooling to room temperature, the pH of the mixture was readjusted to pH>9, and the temperature was increased to 50° C. A sodium silicate solution was added, equivalent to 10% by weight $SiO_2$ on $TiO_2$ weight, whilst keeping the pH above 9. The temperature was maintained at 50° C. during the addition. After re-neutralising to pH 6.5 and stirring for 30 minutes, the mixture was heated to 60° C. and the pH adjusted to pH 9.5. 3-aminopropyl triethoxysilane was added, equivalent to 7.5% on $TiO_2$ weight. The mixture was stirred for 30 minutes, after which the temperature was increased to 75° C. Sodium stearate (equivalent to 7.5% by weight of sodium stearate on $TiO_2$) dissolved in hot water was added.

The slurry was equilibrated for 45 minutes and neutralised by adding 20% hydrochloric acid dropwise over 15 minutes, before the slurry was allowed to cool to less than 50° C. The slurry was filtered using a Buchner filter until the cake conductivity at 100 $gdm^{-3}$ in water was <150 μS. The filter cake was oven-dried for 16 hours at 110° C. and ground into a fine powder by an IKA Werke dry powder mill operating at 3,250 rpm.

A dispersion was produced by mixing 7 g of polyglyceryl-3 polyricinoleate with 53 g of C12-C15 alkylbenzoate, and then adding 40 g of titanium dioxide powder produced above into the mixture. The mixture was passed through a horizontal bead mill, operating at 1500 r.p.m. and containing zirconia beads as grinding media for 15 minutes.

The titanium dioxide particles or dispersion thereof were subjected to the test procedures described herein, and exhibited the following properties;

(a) Dispersion particle size;

i) D (v,0.5)=48 nm, ii) 10% by volume of particles have a volume diameter less than 28 nm, iii) 16% by volume of particles have a volume diameter less than 31 nm, iv) 30% by volume of particles have a volume diameter less than 38 nm, v) 70% by volume of particles have a volume diameter less than 62 nm, vi) 84% by volume of particles have a volume diameter less than 83 nm, and vii) 90% by volume of particles have a volume diameter less than 305 nm.

(b) Extinction coefficients;

| $E_{524}$ | $E_{308}$ | $E_{360}$ | E(max) | λ (max) | $E_{308}/E_{524}$ |
|---|---|---|---|---|---|
| 1.2 | 45.0 | 8.7 | 59.6 | 276 | 38.5 |

(c) BET specific surface area=86.4 $m^2g^{-1}$.

(d) Photogreying index=3.38.

Example 2

The titanium dioxide dispersion produced in Example 1 was used to prepare a sunscreen emulsion formulation having the following composition;

| Trade Name | INCI Name | % w/w |
| --- | --- | --- |
| Phase A | | |
| Cithrol ™ DPHS (ex Croda) | PEG-30 Dipolyhydroxystearate | 2.0 |
| Crodamol ™ IPM (ex Croda) | Isopropyl Myristate | 15.0 |
| Candelilla Wax | *Euphorbia Cerifera* (Candelilla) Wax | 1.0 |
| TiO₂ dispersion produced in Example 1 | | 19.0 |
| Phase B | | |
| Water | Aqua | 57.3 |
| Pricerine ™ 9091 (ex Croda) | Glycerin | 4.0 |
| Magnesium Sulphate Heptahydrate | Magnesium Sulphate Heptahydrate | 0.7 |
| Phase C | | |
| Euxyl K350 | Phenoxyethanol, Methylparaben, Ethylparaben, Ethylhexylglycerin, Propylene Glycol | 1.0 |

Procedure
1. Combine Phase B ingredients with stirring and heat to 75-80° C.
2. Separately, combine Phase A ingredients, except TiO₂ dispersion, and heat to 75-80° C.
3. Add TiO₂ dispersion to Phase A ingredients with stirring, and briefly re-heat to 75-80° C.
4. Add Phase B to Phase A ingredients slowly with intensive stirring.
5. Homogenise for one minute.
6. Once below 40° C. add Phase C and mix until homogeneous.
7. Stir/cool to room temperature.

The emulsion had an SPF value of 14 and exhibited good skin feel. The immediate "afterfeel" was assessed as 19.3% "oily" and 50.2% "waxy". The 20 minute afterfeel was assessed as 3.9% "oily" and 73.2% "waxy"

Example 3

The titanium dioxide dispersion produced in Example 1 was used to prepare a sunscreen emulsion formulation having the following composition;

| Trade Name | INCI Name | % w/w |
| --- | --- | --- |
| Phase A | | |
| Cithrol ™ DPHS (ex Croda) | PEG-30 Dipolyhydroxystearate | 2.5 |
| Arlamol ™ HD (ex Croda) | Isohexadecane | 3.0 |
| Arlamol ™ PS15E (ex Croda) | PPG-15 Stearyl Ether | 1.0 |
| DC 200 Fluid 350 cst | Dimethicone | 2.0 |
| Solaveil ™ CZ-100 (ex Croda) | Zinc oxide | 37.0 |
| TiO₂ dispersion produced in Example 1 | | 3.0 |
| Phase B | | |
| Water | Aqua | 44.7 |
| Pricerine ™ 9091 | Glycerin | 5.0 |
| (ex Croda) | | |
| Magnesium Sulphate Heptahydrate | Magnesium Sulphate Heptahydrate | 0.8 |
| Phase C | | |
| Euxyl PE9010 | Phenoxyethanol | 1.0 |

Procedure
1. Combine Phase B ingredients with stirring and heat to 75-80° C.
2. Separately, combine Phase A ingredients, except TiO₂ dispersion, and Solaveil™ CZ-100 and heat to 75-80° C.
3. Add TiO₂ dispersion to Phase A ingredients, and briefly re-heat to 75-80° C.
4. Add Phase B to Phase A ingredients slowly with intensive stirring.
5. Homogenise for one minute.
6. Once below 40° C. add Phase C and mix until homogeneous.
7. Stir/cool to room temperature.

The emulsion had an SPF value of 28.

Example 4

The titanium dioxide dispersion produced in Example 1 was used to prepare a sunscreen emulsion formulation having the following composition;

| Trade Name | INCI Name | % w/w |
| --- | --- | --- |
| Phase A | | |
| Crodamol ™ GTCC (ex Croda) | Caprylic/Capric triglyceride | 3.0 |
| Crodamol ™ ISIS (ex Croda) | Isostearyl Isostearate | 3.0 |
| Pripure ™ 3759 (ex Croda) | Squalane | 3.0 |
| Crodacol ™ S95 (ex Croda) | Stearyl Alcohol | 2.0 |
| Tinosorb S | Bis-Ethylhexyloxyphenol Methoxyphenyl Triazine | 3.5 |
| Uvinul A | Dethylamine Hydroxybenzoyl Hexyl Benzoate | 2.0 |
| TiO₂ dispersion produced in Example 1 | | 16.0 |
| Phase B | | |
| Water | Aqua | 55.5 |
| Pricerine ™ 9091 (ex Croda) | Glycerin | 3.0 |
| Veegum Ultra | Magnesium Aluminum Silicate | 0.8 |
| Arlacel ™ LC | Sorbitan Stearate (and) Sorbityl Laurate | 3.5 |
| Keltrol SFT | Xanthan Gum | 0.2 |
| Tinosorb M | Methylene Bis-Benzotriazolyl Tetramethylbutylphenol | 3.5 |
| Phase C | | |
| Euxyl K350 | Phenoxyethanol, Methylparaben, Ethylparaben, Ethylhexylglycerin, Propylene Glycol | 1.0 |

Procedure
1. Premix the Keltrol SFT, Veegum Ultra and Pricerine™ 9091, add water with stirring.
2. Add the remaining Phase B ingredients with stirring and heat to 75-80° C.
3. Separately, combine Phase A ingredients, except TiO₂ dispersion, and heat to 75-80° C.
4. Homogenise Phase B ingredients for 30 seconds and allow to swell for 20 minutes at 75-80° C.
5. Add TiO₂ dispersion to Phase A ingredients with stirring, and briefly re-heat to 75-80° C.
4. Add Phase A to Phase B ingredients with stirring.
5. Homogenise for one minute.
6. Once below 40° C. add Phase C and mix until homogeneous.
7. Stir/cool to room temperature.

The emulsion had an SPF value of 41.

The above examples illustrate the improved properties of a particulate metal oxide, dispersion and sunscreen product according to the present invention.

The invention claimed is:

1. Coated metal oxide particles comprising metal oxide core particles each having thereon a coating layer comprising silica, a fatty acid and/or a salt thereof and a silane coupling agent,
wherein
the metal oxide comprises titanium dioxide,
the silane coupling agent comprises at least one hydrolyzable group and an amine group,
the coated metal oxide particles have an $E_{308}/E_{524}$ ratio of greater than 20, and
the coated metal oxide particles have a BET specific surface area in a range from 75 to 100 $m^2g^{-1}$.

2. The coated metal oxide particles of claim 1, wherein the fatty acid has 10 to 24 carbon atoms.

3. The coated metal oxide particles of claim 1, wherein the coating layer comprises 0.5% to 35% by weight of the silica, and/or 0.5 to 20% by weight of silane coupling agent, and/or 0.5% to 20% by weight of fatty acid and/or salt thereof, all based on the weight of the metal oxide core particles.

4. The coated metal oxide particles of claim 1, comprising 82% to 84% by weight of the metal oxide, 6.5% to 7.5% by weight of the silica, 4% to 5.5% by weight of silane coupling agent, and 4.5% to 6% by weight of fatty acid and/or salt thereof, all based on the total dry weight of the particles.

5. The coated metal oxide particles of claim 1, having a median volume particle diameter in dispersion of 40 to 55 nm.

6. The coated metal oxide particles of claim 1, having a BET specific surface area in a range from 85 to 90 $m^2g^{-1}$.

7. The coated metal oxide particles of claim 1, having a maximum extinction coefficient ($E_{max}$) in the range from 50 to 68 l/g/cm.

8. A dispersion comprising the coated metal oxide particles of claim 1 in a liquid dispersing medium, wherein the liquid dispersing medium is a cosmetically acceptable material.

9. The dispersion of claim 8, which comprises at least 30% by weight of the coated metal oxide particles.

10. The dispersion of claim 8, which comprises a dispersing agent.

11. A method of making the coated metal oxide particles of claim 1, comprising:
   (i) forming metal oxide core particles, and
   (ii) applying a coating layer to the metal oxide core particles comprising silica, the silane coupling agent, and the fatty acid and/or salt thereof.

12. The method of claim 11, wherein the coating layer is applied sequentially in the order of (1) silica, (2) silane coupling agent, and (3) fatty acid and/or salt thereof.

13. A sunscreen composition comprising the coated metal oxide particles of claim 1.

14. A method of improving skin feel in a sunscreen composition comprising applying to the skin a composition comprising coated metal oxide particles of claim 1.

15. The method of claim 14, wherein the improved skin feel includes a higher degree of lubricity to the skin.

16. A composition comprising:
   (i) coated metal oxide particles comprising metal oxide core particles each having thereon a coating layer comprising silica, a fatty acid and/or a salt thereof and a silane coupling agent,
   wherein
      the metal oxide comprises at least one member selected from the group consisting of titanium dioxide, zinc oxide and iron oxide,
      the silane coupling agent comprises at least one hydrolyzable group and an amine group, and
      the coated metal oxide particles have a BET specific surface area in a range from 75 to 100 $m^2g^{-1}$; and
   (ii) a liquid medium selected from the group consisting of a C12-C15 alkyl benzoate, a fatty acid glyceride and isohexadecane.

* * * * *